United States Patent
Finze et al.

(10) Patent No.: US 8,436,199 B2
(45) Date of Patent: May 7, 2013

(54) STRONG BORON-CONTAINING ACIDS, THE PREPARATION AND USE THEREOF

(75) Inventors: Maik Finze, Nienburg (DE); Eduard Bernhardt, Wuppertal (DE); Helge Willner, Muelheim/Ruhr (DE); Nikolai (Mykola) Ignatyev, Duisburg (DE); Urs Welz-Biermann, Heppenheim (DE)

(73) Assignee: Merck Patent GmbH, Darmstadt (DE)

( * ) Notice: Subject to any disclaimer, the term of this patent is extended or adjusted under 35 U.S.C. 154(b) by 624 days.

(21) Appl. No.: 12/625,648

(22) Filed: Nov. 25, 2009

(65) Prior Publication Data

US 2010/0069655 A1 Mar. 18, 2010

Related U.S. Application Data

(63) Continuation of application No. 11/665,739, filed on Apr. 20, 2007.

(51) Int. Cl.
*C07F 5/02* (2006.01)
(52) U.S. Cl.
USPC .............................................. 558/384; 568/1
(58) Field of Classification Search ................... 558/384
See application file for complete search history.

(56) References Cited

U.S. PATENT DOCUMENTS

2006/0222584 A1 10/2006 Welz-Biermann et al.

FOREIGN PATENT DOCUMENTS

WO WO 2004/072089 A 8/2004

OTHER PUBLICATIONS

Maik Finze et al, (CF3) 3BCP!-and ¹ (CF3)3BACs!-: Thermally Stable Phosphaethynyl and Arsaethynyl Complexes, Angewandte Chemie, International Addition, Aug. 13, 2004, pp. 1433-7851, 43(32), Columbus, OH, USA.
Bernhardt E. et al., Eine Effiziente Synthete Von Tetracyanoboratent Durch Sinterprozess "An Efficient Synthesis for Tetracyanoborates by Sinter Processes", 2003, Bd. 629, pp. 1229-1234.
Jiao, et al., Large Effects of Medium on Geometries. An ab Initio Study, Journal of The American Chemical Society, 1994, pp. 7429-7439, 116(16).
Hamilton et al., The Structures of Cu(I) and AG(I) Coordination Polymers Using the Tricyanofluoroborate Anion, Chem. Comm., 2002 pp. 842-843.
Zhou et al., "A new class of hydrophobic ionic liquids: Trialkyl(2-methoxyethyl)ammonium Perfluoroethyltrifluoroborate", Chemistry Letters (2004), 33(7), 886-887.
Buerger et al., "The reaction of boron trihalides with trimethylstannyltrifluoromethane in the presence of trimethylamine", Journal of Fluorine Chemistry (1985), 28(2), 183-189.
Bernhardt et al., The reactions of M[BF4] (M = Li, K) and (C2H4)2O. BF3 with (CH3)3SICN, Formation of M[BFx(CN)4-x] (M = Li, K; x= 1, 2) and (CH3)3SiNCBFx(CN)3-x, (x = 0, 1), Zeitschrift fuer Anorganische and Allgemeine Chemie (2003), 629(4), 677-685.

*Primary Examiner* — Johann Richter
*Assistant Examiner* — Kofi Adzamli
(74) *Attorney, Agent, or Firm* — Millen, White, Zelano & Branigan, P.C.

(57) ABSTRACT

The invention relates to boron-containing acids of the general formula (I) $[B(R^F)_{4-x-y}(CN)_x F_y]^- H^+$ (I), where x=0, 1, 2, 3 or 4, y=0, 1, 2 or 3 x+y≦4, and in which the ligands $R^F$ may be identical or different and $R^F$ stands for a perfluorinated or partially fluorinated $C_{1-12}$-alkyl group and where the CN group is bonded to the B atom via the C atom, and complexes thereof with a solvent, to salts comprising a cation and the anion of a selection of the acids according to the invention, and to processes for the preparation of the salts.

5 Claims, No Drawings

STRONG BORON-CONTAINING ACIDS, THE PREPARATION AND USE THEREOF

This application is a continuation of U.S. application Ser. No. 11/665,739, filed on Apr. 20, 2007.

The invention relates to boron-containing acids of the general formula (I)

$$[B(R^F)_{4-x-y}(CN)_xF_y]^-H^+ \qquad (I)$$

where
x=0, 1, 2, 3 or 4,
y=0, 1, 2 or 3 and
x+y≦4,
and in which
the ligands $R^F$ may be identical or different and
$R^F$ stands for a perfluorinated or partially fluorinated $C_{1-12}$-alkyl group and
where the CN group is bonded to the B atom via the C atom,
and complexes thereof with a solvent.

The present invention furthermore relates to processes for the preparation of the acids according to the invention, to salts comprising a cation and the anion of a selection of the acids according to the invention, and to processes for the preparation of the salts.

The invention furthermore relates to the use of the acids and salts according to the invention.

The prior art describes borate anions in which fluorine ligands have been replaced by cyanide (E. Bernhardt, G. Henkel, H. Willner, Z. Anorg. Allg. Chem. 626 (2000) 560; D. Williams, B. Pleune, J. Kouvetakis, M. D. Williams, R. A. Andersen, J. Amer. Chem. Soc. 122 (2000) 7735; E. Bernhardt, M. Berkei, M. Schürmann, H. Willner, Z. Anorg. Allg. Chem. 628 (2002) 1734) and trifluoromethyl ligands (E. Bernhardt, G. Henkel, H. Willner, G. Pawelke, H. Bürger, Chem. Eur. J. 7 (2001) 4696; G. Pawelke, H. Bürger, Coord. Chem. Rev. 215 (2001) 243). The trifluoromethyl borates here are synthesised starting from the cyanoborates, but the cyanoborates are accessible with difficulty and only in small amounts. The synthesis of $[B(CN)_4]^-$ is labour-intensive and can only be carried out on a small preparative scale. In addition, the starting materials are expensive. Salts with tetrakis(trifluoromethyl)borate anions are described in EP 1205480 A1. A novel synthesis of alkali metal tetracyanoborates and salts, in particular ionic liquids, with a cyanoborate anion which also contains F ligands are described in WO 2004/07089.

The synthesis of the cyanoboric acids of the formula (I) in which replacement of a cyanide ligand by a perfluoroalkyl ligand is carried out in the simultaneous presence or absence of a fluoride ligand has not been carried out to date.

The present invention had the object of providing alternative strong acids which can be used, in particular, for the synthesis of salts which lead to ionic liquids or catalyst systems.

This object is achieved by the acids of the general formula (I)

$$[B(R^F)_{4-x-y}(CN)_xF_y]^-H^+ \qquad (I)$$

where
x=0, 1, 2, 3 or 4,
y=0, 1, 2 or 3 and
x+y≦4.
and in which
the ligands $R^F$ may be identical or different and
$R^F$ stands for a perfluorinated or partially fluorinated $C_{1-12}$-alkyl group and where the CN group may be bonded to the B atom via the C atom,
and complexes thereof with a solvent.

Fluorinated alkyl groups are, for example, difluoromethyl, trifluoromethyl, pentafluoroethyl, pentafluoropropyl, heptafluoropropyl, pentafluorobutyl, heptafluorobutyl, nonafluorobutyl, $C_5H_4F_7$, $C_5H_2F_9$, $C_5F_{11}$, $C_6H_4F_9$, $C_6H_2F_{11}$, $C_6F_{13}$, $C_7H_4F_{11}$, $C_7H_2F_{13}$, $C_7F_{15}$, $C_8H_4F_{13}$, $C_8H_2F_{15}$, $C_8F_{17}$, $C_9H_4F_{15}$, $C_9H_2F_{17}$, $C_9F_{19}$, $C_{10}H_4F_{17}$, $C_{10}H_2F_{19}$, $C_{10}F_{21}$, $C_{11}H_4F_{19}$, $C_{11}H_2F_{21}$, $C_{11}F_{23}$, $C_{12}H_4F_{21}$, $C_{12}H_2F_{23}$ or $C_{12}F_{25}$. Perfluoroalkyl group means that all H atoms of the alkyl group, as described above, have been replaced by F atoms. Fluorinated means that 1 to 16 fluorine atoms in a perfluoroalkyl group have been replaced by hydrogen atoms.

Preference is given to acids in which the ligands $R^F$ are identical and stand for a perfluorinated $C_{1-4}$-alkyl group. $R^F$ is particularly preferably trifluoromethyl or pentafluoroethyl.

Preference is furthermore given to acids in which y=0.

Very particular preference is given to the acids according to the invention tetracyanoboric acid monohydrate $[B(CN)_4]^-H^+ \cdot H_2O$, tris(trifluoromethyl)cyanoboric acid, $[(CF_3)_3BCN]^-H^+$ tris(trifluoromethyl)cyanoboric acid diethyl etherate, $[(CF_3)_3BCN]^-H^+\cdot (C_2H_5)_2O$ or tetrakis(trifluoromethyl)boric acid bis(diethyl etherate), $[B(CF_3)_4]^-H^+\cdot 2(C_2H_5)_2O$.

The present invention furthermore relates to processes for the preparation of the acids according to the invention.

The synthesis of the boric acids of the formula I

$$[B(R^F)_{4-x-y}(CN)_xF_y]^-H^+ \qquad (I),$$

where
x=0, 1, 2, 3 or 4 and
y=0, 1, 2 or 3 and
x+y≦4
and in which
the ligands $R^F$ may be identical or different and
$R^F$ stands for a perfluorinated or partially fluorinated $C_{1-12}$-alkyl group,
and complexes thereof with a solvent,
is carried out by reaction of alkali metal salts of the formula (II-1)

$$[B(R^F)_{4-x-y}(CN)_xF_y]_a^-M^{a+} \qquad (II-1)$$

x=0, 1, 2, 3, or 4,
y=0, 1, 2 or 3 and
x+y≦4,
a=1,
and in which
$R^F$ may be identical or different and
$R^F$ stands for a the ligands perfluorinated or partially fluorinated $C_{1-12}$-alkyl group and
$M^{a+}$ is an alkali metal cation, with
an acid, where conversion into the trialkylsilyl ether may optionally be carried out in advance, in particular in the case of later reaction with anhydrous HF.

The synthesis of the alkali metal compounds of the formula (II-1) containing at least one cyano group is carried out by isomerisation of corresponding isocyanoborate salts at temperatures between 150° and 300° C., preferably 200°-250° C. The isocyanate borate salts of the formula (II-2)

$$[B(R^F)_{4-x-y}(NC)_xF_y]_a^-M^{a+} \qquad (II-2)$$

x=0, 1, 2, 3 or 4,
y=0, 1, 2 or 3
x+y≦4
a=1, and in which

R$^F$ may be identical or different and

R$^F$ stands for a the ligands perfluorinated or partially fluorinated C$_{1-12}$-alkyl group and M$^{a+}$ is an alkali metal cation, are formed by reaction of the corresponding isocyanoboric acid with a strong base.

Suitable bases are, for example, alkali metal amides, such as M[N(SiMe$_3$)], where M may denote lithium, sodium or potassium.

The first step of this reaction is advantageously carried out in toluene, benzene, hexane or pentane, particularly preferably in toluene, at −60° to 0° C., preferably at −20° C.

The tetracyanoboric acid is synthesised, for example, under the conditions indicated in Example 4.

In general, the acids of the formula (I) are formed from the reaction of the corresponding metal salts, in particular alkali metal salts, with strong acids, for example hydrochloric acid.

The metal salts of the acids of the formula (I) can be obtained, for example, by the following two-step reaction:

Potassium tetrafluoroborate can be reacted with NaCN in the presence of KCl to give the salts potassium tetracyanoborate as principal product, as described in WO 2004/07089, but with the salts K[B(CN)$_3$ F], K[B(CN)$_2$ F$_2$]and K[B(CN)F$_3$] also being formed in different amount ratios. Stepwise replacement of the fluorine ligand by the CN ligand enables control of the ligand exchange and the amount ratios of the salts formed via the reaction time and does not present the person skilled in the art with any difficulties. The subsequent reaction with ClF$_3$, ClF or (CH$_3$)$_2$NF, as described in J. Am. Chem. Soc. 2002, 124, 15385-15398, results, for example, in the salts K[B(CF$_3$)$_4$], K[B(CF$_3$)$_3$CN], K[B(CF$_3$)$_3$F], K[B(CF$_3$)$_2$CNF] or K[B(CF$_3$)CNF$_2$] in different amount ratios. The amount ratio of the reaction products can be controlled by the way in which the reaction is carried out.

The acids of the formula (I) which contain at least one CN group can be isolated as solvent-free acids. The acids of the formula (I) in which x=0 require the solvent in order to solvate the proton and thus stabilise the structure.

The acids according to the invention have high proton activity, as can be seen, for example, through deuterium exchange in C$_6$ D$_6$.

The acids according to the invention can be used for the synthesis of further inorganic or organic salts, which can in turn be used as conductive salts for various electrochemical devices or as ionic liquids. The conversion into their salts is carried out, for example, by neutralisation using an inorganic or organic base, for example the reaction of tetracyanoboric acid with tetra(butyl)ammonium hydroxide to give tetra(butyl)ammonium tetracyanoborate.

The acids according to the invention or the inorganic salts thereof, in particular alkali metal salts, are also good starting materials for cationic dyes containing the cyanoborate anions of the formula [B(R$^F$)$_{4-x-y}$(CN)$_x$F$_y$]$^-$, where x, y and R$^F$ have a meaning indicated above.

The present invention furthermore relates to a selection of salts of the acids of the formula (I) according to the invention, namely the salts of the general formula (II)

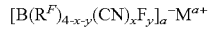

[B(R$^F$)$_{4-x-y}$(CN)$_x$F$_y$]$_a^-$M$^{a+}$  (II)

where
x=1, 2 or 3,
y=0 or 1,
x+y≦4,
a=1 or 2,
and in which
the ligands R$^F$ may be identical or different and R$^F$ stands for a perfluorinated or partially fluorinated C$_{1-12}$-alkyl group and where the CN group is bonded to the B atom via the C atom and M$^{a+}$ is an alkali metal cation, a silver, magnesium, copper(I), copper(II), zinc(II) or calcium(II) cation or an organic cation, where K[B(CF$_3$)$_3$CN] and [NH$_4$][B(CF$_3$)$_3$CN] are excluded.

Preference is given in accordance with the invention to a group of the salts of the formula (II) in which y=0.

Preference is given in accordance with the invention to a group of compounds of the formula (II) in which the cation M$^{a+}$ is an alkali metal cation, preferably a lithium, sodium or potassium cation.

This group of compounds of the formula (II) is particularly suitable for the synthesis of ionic liquids containing the anion [B(R$^F$)$_{4-x-y}$(CN)$_x$F$_y$]$_a^-$, where x, y, a and R$^F$ have a meaning indicated above, by metathesis with a salt MA, consisting of an organic cation, as defined below, and the counterion A, defined as F$^-$, C$^-$, Br$^-$, I$^-$, OH$^-$, [HF$_2$]$^-$, [CN]$^-$, [SCN]$^-$, [CH$_3$COO]$^-$, [CH$_3$ SO$_3$]$^-$, [CF$_3$ COO]$^-$, [CF$_3$ SO$_3$]$^-$, [CH$_3$OSO$_3$]$^-$, [SiF$_6$]$^{2-}$, [BF$_4$]$^-$, [SO$_4$]$^{2-}$[HSO$_4$]$^{1-}$, [NO$_3$]$^-$, [C$_2$H$_5$OSO$_3$]$^-$, [(C$_2$ F$_5$)$_2$P(O)O]$^-$, [C$_2$ F$_5$P(O)O$_2$]$^{2-}$, tosylates, malonates, substituted malonates or [CO$_3$]$^{2-}$, where electroneutrality must be ensured in the formula of the salt MA. The anion is preferably F$^-$, Cl$^-$, Br$^-$, I$^-$, [HF$_2$]$^-$, [CH$_3$ SO$_3$]$^-$[CH$_3$ OSO$_3$]$^-$,[CF$_3$COO]$^-$,[CF$_3$ SO$_3$]$^-$,[(C$_2$F$_5$)$_2$P(O)O]$^-$ or [CO$_3$]$^{2-}$, particularly preferably Cl$^-$, Br$^-$, [CH$_3$ OSO$_3$]$^-$, [CH$_3$ SO$_3$]$^-$, [CF$_3$ SO$_3$]$^-$ or [(C$_2$ F$_5$)$_2$ P(O)O]$^-$.

The lithium compounds in this group are particularly suitable as conductive salts in electrolytes, primary batteries, secondary batteries, capacitors, supercapacitors or electrochemical cells, optionally also in combination with further conductive salts and/or additives, as constituent of a polymer electrolyte or phase-transfer agent.

Preference is given in accordance with the invention to a group of compounds of the formula (II) in which the cation M$^{a+}$ is a silver, magnesium, copper(1), copper(II), zinc(II) or calcium(II) cation. The magnesium, copper(II), zinc(II) or calcium(II) cations are preferably in solvated form.

This group of compounds is likewise suitable for the synthesis of ionic liquids containing the corresponding anion by metathesis with a salt MA, as described above for the compounds of the formula (II) containing alkali metal cations.

This group of compounds is particularly suitable for metal deposition or as phase-transfer agent.

Preference is given in accordance with the invention to a group of compounds of the formula (II) in which the cation M$^{a+}$ is an organic cation.

The organic cation here can be selected from the group [NR$^1$R$^2$R$^3$R$^4$]$^+$, [PR$^1$R$^2$R$^3$R$^4$]$^+$, [P(NR$^1$R$^2$)$_2$(NR$^3$R$^4$)$_2$]$^+$, [C(NR$^1$R$^2$)(NR$^3$R$^4$)(NR$^5$R$^6$)]$^+$, [(R$^1$R$^2$N)C(=OR$^7$)(NR$^3$R$^4$)]$^+$, [(R$^1$R$^2$N)C(=SR$^7$)(NR$^3$R$^4$)]$^+$ or [(C$_6$H$_6$)$_3$ C]$^+$, where the phenyl groups of the tritylium may each be substituted, independently of one another, by R$^1$ to R$^4$.

R$^1$ to R$^7$ each, independently of one another, denotes hydrogen or straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more, but not all, substituents R$^1$ to R$^7$ may be partially or fully substituted by halogens, in particular —F and/or —Cl, or partially by —CN or —NO$_2$ and where, in the substituents $R^1$ to $R^6$, one or two non-adjacent carbon atoms which are not in the α-position may be replaced by atoms and/or atom groups selected from the group —O—, —C(O)—, —C(O)O—, —S—, —S(O)—, —SO$_2$—, —SO$_2$O—, —C(O)NH—, —C(O)NR'—, —SO$_2$ NH—, —SO$_2$ NR'—, —N=, —N=N—, —NH—, —NR'—, —PR'—, —P(O)R'—, —P(O)R'—O—, —O—P(O)R'—O—, —P(O)(NR'$_2$)—NR'— and —PR'$_2$=N— or by the end groups —C(O)X' or —SO$_2$X', where R'=non-, partially or perfluorinated $C_1$- to $C_6$-alkyl, $C_3$- to $C_7$-cycloalkyl, unsubstituted or substituted phenyl or an unsubstituted or substituted heterocycle, and X'=F, Cl or Br.

An alkyl group having 1 to 20 C atoms is taken to mean, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, $C_{11}H_{23}$, $C_{12}H_{25}$, $C_{13}H_{27}$, $C_{14}H_{29}$, $C_{15}H_{31}$, $C_{16}H_{33}$, $C_{17}H_{35}$, $C_{18}H_{37}$, $C_{19}H_{39}$ or $C_{20}H_{41}$. The alkyl groups may also be partially or fully substituted by halogens, in particular —F and/or —Cl. Fluorinated alkyl groups are difluoromethyl, trifluoromethyl, pentafluoroethyl, pentafluoropropyl, heptafluoropropyl, heptafluorobutyl or nonafluorobutyl.

A straight-chain or branched alkenyl having 2 to 20 C atoms, where a plurality of double bonds may also be present, is, for example, allyl, 2- or 3-butenyl, isobutenyl, sec-butenyl, furthermore 4-pentenyl, isopentenyl, hexenyl, heptenyl, octenyl, —C$_9$H$_{17}$, —C$_{10}$H$_{19}$ to —C$_{20}$H$_{39}$; preferably allyl, 2- or 3-butenyl, isobutenyl, sec-butenyl, preference is furthermore given to 4-pentenyl, isopentenyl or hexenyl.

A straight-chain or branched alkynyl having 2 to 20 C atoms, where a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —C$_9$H$_{15}$, —C$_{10}$H$_{17}$ to —C$_{20}$H$_{37}$, preferably ethynyl, 1- or 2-propynyl, 2- or 3-butynyl, 4-pentynyl, 3-pentynyl or hexynyl.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by $C_1$- to $C_6$-alkyl groups, where the cycloalkyl group or the cycloalkyl group which is substituted by $C_1$- to $C_6$-alkyl groups may in turn also be substituted by halogen atoms, such as F, Cl, Br or I, in particular F or Cl, CN or NO$_2$.

The substituents $R^1$ to $R^7$ may be partially or fully substituted by halogen atoms, in particular by F and/or Cl, or partially by CN or NO$_2$.

Furthermore, the substituents $R^1$ to $R^6$ may be replaced by one or two non-adjacent heteroatoms or atom groups selected from the group —O—, —C(O)—, —C(O)O—, —S—, —S(O)—, —SO$_2$—, —SO$_2$O—, —C(O)NH—, —C(O)NR'—, —SO$_2$ NH—, —SO$_2$ NR'—, —N=, —N=N—, —NH—, —NR'—, —PR'—, —P(O)R'—, —P(O)R'—O—, —O—P(O)R'—O—, —P(O)(NR'$_2$)—NR'— and —PR'$_2$=N— or by the end groups —C(O)X' or —SO$_2$X', where R'=non-, partially or perfluorinated $C_1$- to $C_6$-alkyl, $C_3$- to $C_7$-cycloalkyl, unsubstituted or substituted phenyl or an unsubstituted or substituted heterocycle, and X'=F, Cl or Br, which are not in the α-position to a nitrogen atom or phosphorus atom.

In R', $C_3$- to $C_7$-cycloalkyl is, for example, cyclopropyl, cyclobutyl, cyclopentyl, cyclohexyl or cycloheptyl.

In R', substituted phenyl denotes phenyl which is substituted by $C_1$- to $C_6$-alkyl, $C_1$- to $C_6$-alkenyl, NO$_2$, F, Cl, Br, I, OH, $C_1$-$C_6$-alkoxy, CN, SCN, SCF$_3$, SO$_2$ CF$_3$, C(O)O—$C_1$-$C_6$-alkyl, NH$_2$, $C_1$-$C_6$-alkylamino or $C_1$-$C_6$-dialkylamino, COOH, C(O)NH$_2$, C(O)NHR", C(O)NR"$_2$, SO$_2$ OR", SO$_2$X', SO$_2$ NH$_2$, SO$_2$ NHR", SO$_2$ NR"$_2$, SO$_3$H, NR"C(O)R" or NHC(O)R", where X' denotes F, Cl or Br and R" denotes a non-, partially or perfluorinated $C_1$- to $C_6$-alkyl or $C_3$- to $C_7$-cycloalkyl, as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-aminophenyl, o-, m- or p-(N,N-dimethylamino)phenyl, o-, m- or p-nitrophenyl, o-, m- or p-hydroxyphenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, further preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In R', heterocycle is taken to mean a saturated or unsaturated mono- or bicyclic heterocyclic radical having 5 to 13 ring members, in which 1, 2 or 3 N and/or 1 or 2 S or O atoms may be present and the heterocyclic radical may be mono- or polysubstituted by $C_1$- to $C_6$-alkyl, $C_1$- to $C_6$-alkenyl, NO$_2$, F, Cl, Br, I, OH, $C_1$-$C_6$-alkoxy, CN, SCN, SCF$_3$, SO$_2$CF$_3$, C(O)O—$C_1$-$C_6$-alkyl, NH$_2$, $C_1$-$C_6$-alkylamino or $C_1$-$C_6$-dialkylamino, COOH, C(O)NH$_2$, C(O)NHR", C(O)NR"$_2$, SO$_2$ OR", SO$_2$X', SO$_2$ NH$_2$, SO$_2$ NHR", SO$_2$ NR"$_2$, SO$_3$H, NR"C(O)R" or NHC(O)R", where X' and R" have an above-mentioned meaning.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazoly, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Without restricting generality, examples of substituents $R^1$ to $R^6$ or also below of the substituents $R^{1'}$ to $R^{4'}$ are: —CH$_3$, —C$_2$H$_5$, —C$_3$H$_7$, —CH(CH$_3$)$_2$, —C$_4$H$_9$, —C(CH$_3$)$_3$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{12}$H$_{25}$, —C$_{20}$H$_{41}$, —CH$_2$OCH$_3$, —C$_2$H$_4$OCH(CH$_3$)$_2$, —C$_2$H$_4$C$_2$H$_5$, —C$_2$H$_4$SCH(CH$_3$)$_2$, —CH$_2$ SO$_2$ CH$_3$, —CH$_2$N(H)C$_2$H$_5$, —C$_2$H$_4$N(H)C$_2$H$_5$, —CH$_2$N(CH$_3$)CH$_3$, —CN, —C$_2$H$_4$N(CH$_3$)CH$_3$, —CF$_3$, —C$_2$ F$_5$, —C$_3$ F$_7$, —C$_4$ F$_9$, —C(CF$_3$)$_3$, —CH$_2$ SO$_2$ CF$_3$, —CF$_2$ SO$_2$ CF$_3$, —C$_2$ F$_4$N(C$_2$ F$_5$)C$_2$ F$_5$, —CHF$_2$, —CH$_2$ CF$_3$, C$_2$F$_4$H, —C$_2$F$_2$H$_3$, —C$_3$FH$_6$, —CH$_2$C$_3$F$_7$, —C(CFH$_2$)$_3$, —CH$_2$C(O)OH, —CH$_2$C$_6$H$_5$, —CH$_2$C(O)CH$_3$, —CH$_2$C(O)C$_2$H$_5$, —CH$_2$C(O)OCH$_3$, CH$_2$C(O)OC$_2$H$_5$, —C(O)CH$_3$, —C(O)C$_6$H$_5$, —C(O)OCH$_3$, —C(O)OC$_2$H$_5$,

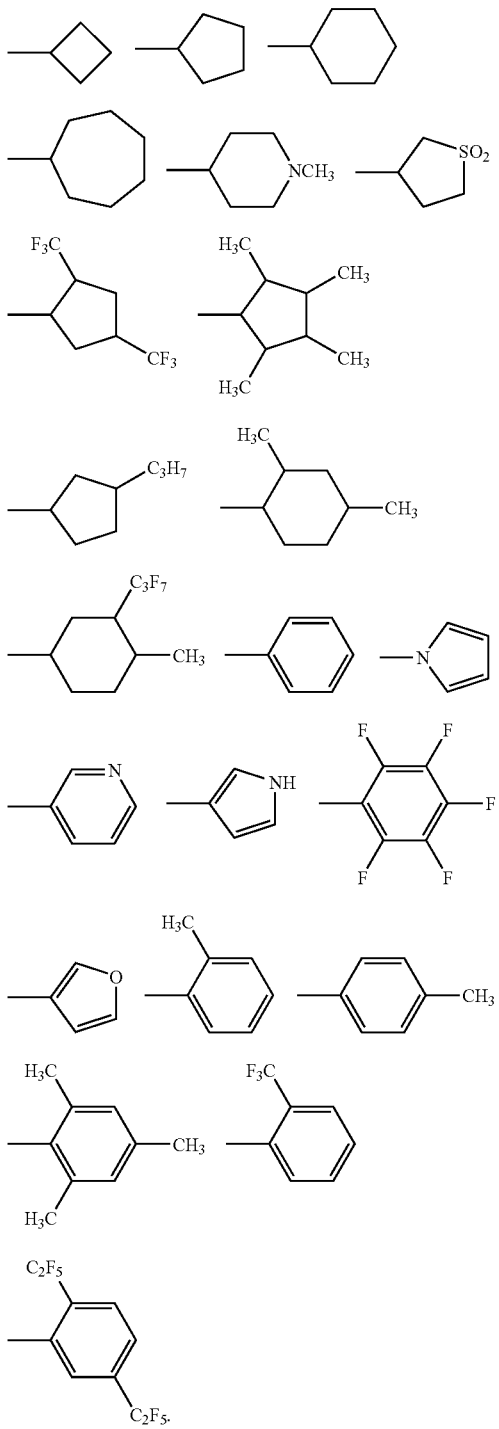

Up to four substituents of the guanidinium cation [C(NR$^1$R$^2$)(NR$^3$R$^4$)—(NR$^5$R$^6$)]$^+$ may also be connected in pairs in such a way that mono-, bi- or polycyclic cations are formed.

Without restricting generality, examples of such guanidinium cations are:

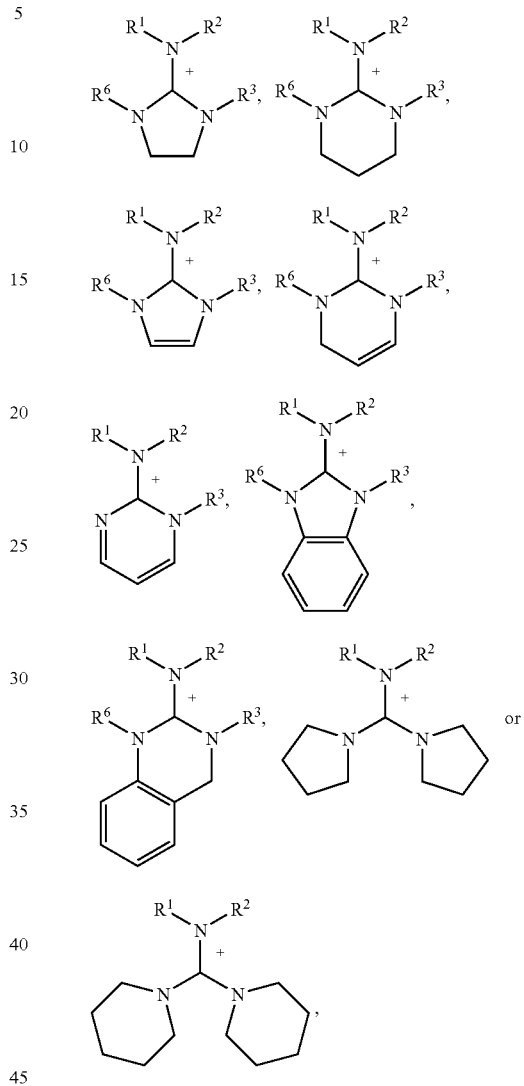

where the substituents R$^1$ to R$^3$ and R$^6$ may have an above-mentioned or particularly preferred meaning.

The carbocycles or heterocycles of the above-mentioned guanidinium cations may optionally also be substituted by C$_1$- to C$_6$-alkyl, C$_1$- to C$_6$-alkenyl, NO$_2$, F, Cl, Br, I, OH, C$_1$-C$_6$-alkoxy, CN, SCN, SCF$_3$, SO$_2$CF$_3$, C(O)O—C$_1$-C$_6$-alkyl, NH$_2$, C$_1$-C$_6$-alkylamino or C$_1$-C$_6$-dialkylamino, COOH, C(O)NH$_2$, C(O)NHR'', C(O)NR''$_2$, SO$_2$OR'', SO$_2$NH$_2$, SO$_2$NHR'', SO$_2$NR''$_2$, SO$_2$X', SO$_3$H, NR''C(O)R'' or NHC(O)R'', where X' and R'' have an above-mentioned meaning, substituted or unsubstituted phenyl or an unsubstituted or substituted heterocycle.

Up to four substituents of the uronium cation [(R$^1$R$^2$N)—C(=OR$^7$)(NR$^3$R$^4$)]$^+$ or of the thiouronium cation [(R$^1$R$^2$N)—C(=SR$^7$)(NR$^3$R$^4$)]$^+$ may also be connected in pairs in such a way that mono-, bi- or polycyclic cations are formed. Without restricting generality, examples of such cations are indicated below, where X=O or S:

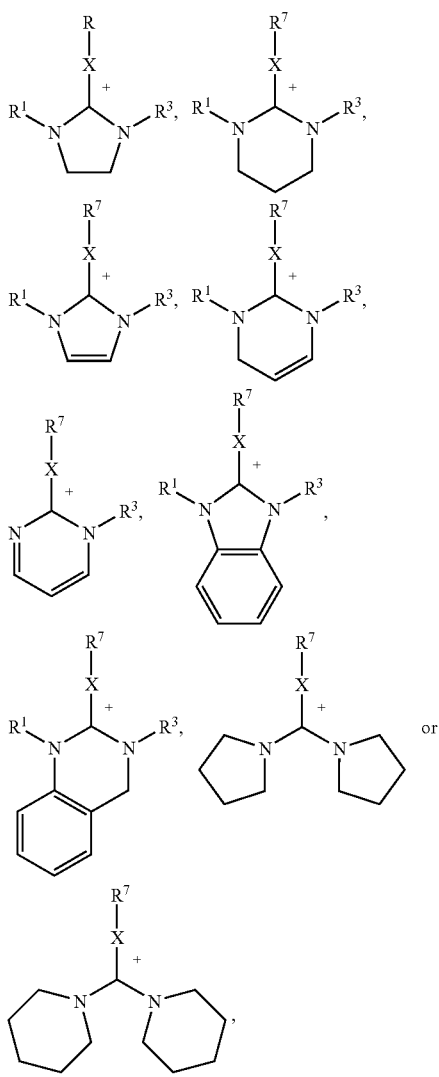

where the substituents R¹, R³ and R⁷ may have an above-mentioned or particularly preferred meaning.

The carbocycles or heterocycles of the above-mentioned cations may optionally also be substituted by $C_1$- to $C_6$-alkyl, $C_1$- to $C_6$-alkenyl, $NO_2$, F, Cl, Br, I, OH, $C_1$-$C_6$-alkoxy, CN, SCN, $SCF_3$, $SO_2CF_3$, $C(O)O$—$C_1$-$C_6$-alkyl, $NH_2$, $C_1$-$C_6$-alkylamino or $C_1$-$C_6$-dialkylamino, COOH, $C(O)NH_2$, $C(O)$NHR", $C(O)NR"_2$, $SO_2$ OR", $SO_2$ $NH_2$, $SO_2$ NHR", $SO_2$ NR"$_2$, $SO_2X'$, $SO_3H$, NR"C(O)R" or NHC(O)R" or substituted or unsubstituted phenyl or an un-substituted or substituted heterocycle, where X' and R" have an above-mentioned meaning.

The organic cation is particularly preferably selected from the group of the ammonium, phosphonium or guanidinium salts.

The substituents R¹ to R⁷ are each, independently of one another, preferably a straight-chain or branched alkyl group having 1 to 4 C atoms. R¹ to R⁴ are particularly preferably methyl, ethyl, propyl, i-propyl or butyl.

The substituents R¹ to R⁴ in the formulae [NR¹R²R³R⁴]⁺ or [PR¹R²R³R⁴]⁺ are particularly preferably identical.

The organic cation can furthermore be selected from the group of the heterocyclic cations. Heterocyclic cations are, for example,

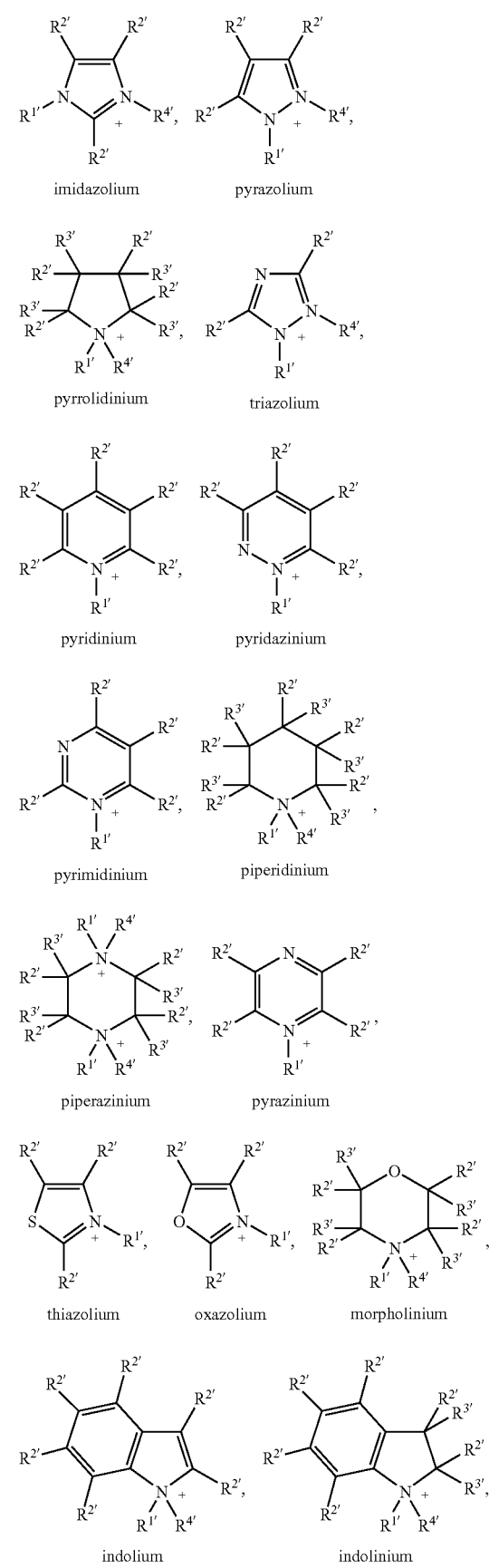

-continued

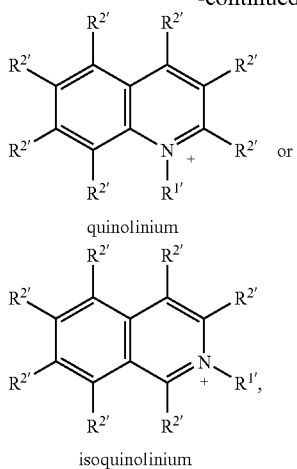

quinolinium isoquinolinium where the substituents

R$^{1\prime}$ to R$^{4\prime}$ each, independently of one another, denotes hydrogen, straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, saturated, partially or fully unsaturated heteroaryl, heteroaryl-C$_1$-C$_6$-alkyl or aryl-C$_1$-C$_6$-alkyl, where one or more substituents R$^{1\prime}$ to R$^{4\prime}$ may be partially or fully substituted by halogens, in particular —F and/or —Cl, or partially by —CN or —NO$_2$, where R$^{1\prime}$ and R$^{4\prime}$ cannot simultaneously be perfluorinated or perchlorinated.

and where, in the substituents R$^{1\prime}$ to R$^{4\prime}$, one or two non-adjacent carbon atoms which are not in the α-position may to the heteroatom be replaced by atoms and/or atom groups selected from the group —O—, —C(O)—, —C(O)O—, —S—, —S(O)—, —SO$_2$—, —SO$_2$O—, —C(O)NH—, —C(O)NR'—, —SO$_2$ NH—, —SO$_2$ NR'—, —N=, —N=N—, —NH—, —NR'—, —PR'—, —P(O)R'—, —P(O)R'—O—, —O—P(O)R'—O—, —P(O)(NR'$_2$)—NR'— and —PR'$_2$=N— or by the end groups —C(O)X' or —SO$_2$X', where R'=non-, partially or perfluorinated C$_1$- to C$_6$-alkyl, C$_3$- to C$_7$-cycloalkyl, unsubstituted or substituted phenyl or an unsubstituted or substituted heterocycle, and X'=F, Cl or Br.

Aryl denotes unsubstituted or substituted phenyl or naphthyl, preferably phenyl.

Aryl-C$_1$-C$_6$-alkyl denotes, for example, benzyl, phenylethyl, phenylpropyl, phenylbutyl, phenylpentyl or phenylhexyl. Fluorinated aryl-C$_1$-C$_6$-alkyl denotes, for example, pentafluorophenyldifluoromethyl, pentafluorophenyltetrafluoroethyl or pentafluorophenylethyl.

The term heteroaryl is identical with the term heterocyclic radical, as described above. A substituent with the name heteroaryl-C$_1$-C$_6$-alkyl is composed of a heteroaryl, as described above, and an alkylene chain having 1 to 6 C atoms, as already described clearly in the case of the term aryl-C$_1$-C$_6$-alkyl.

The substituents R$^{1\prime}$ to R$^{4\prime}$ are particularly preferably a straight-chain or branched alkyl group having 1 to 20 C atoms, very particularly preferably having 1 to 12 C atoms.

From the group of heterocyclic organic cations, the cations are particularly preferably selected from substituted imidazolium, substituted pyridinium, substituted pyrrolidinium, substituted piperidinium or substituted morpholinium, as defined above.

The salts of the formula (II) according to the invention containing organic cations, as described above, can be used as ionic liquids. Ionic liquids can be employed, for example, as solvents for many synthetic or catalytic reactions, for example Friedel-Crafts acylation and alkylation, Diels-Alder cycloadditions, hydrogenation and oxidation reactions, Michael-type reactions or Heck reactions, as non-aqueous electrolytes, which are optionally employed in combination with other conductive salts additives and solvents known to the person skilled in the art.

In addition, these ionic liquids can be used as nonaqueous polar substances in suitable reactions as phase-transfer catalyst, as surfactant (surfaceactive agent), as plasticiser or as medium for the heterogenisation of homogeneous catalysts.

They are furthermore suitable as desiccants, heat-transfer media and as separating agents for gases.

Salts of the formula (II) where M$^{a+}$ is an alkali metal cation can in turn be prepared by neutralising an acid of the formula (Ia), a selection of the acids of the formula (I) according to the invention, $$[B(R^F)_{4-x-y}(CN)_xF_y]^-H^{a+} \quad (Ia)$$

where x=1, 2 or 3, y=0 or 1, x+y≦4 and in which the ligands R$^F$ may be identical or different and

R$^F$ stands for a perfluorinated or partially fluorinated C$_{1-12}$-alkyl group and where the CN group is bonded to the B atom via the C atom using a base containing an alkali metal cation, or by a saltexchange reaction by, for example, subjecting an Li salt of the formula (II) to aqueous work-up using KOH/H2O.

Suitable bases are inorganic bases, such as alkali metal hydroxides, for example KOH, or organic bases, such as alkali metal alkoxides, butyllithium or metal amides, for example MN(SiMe$_3$), where Me=methyl and M=Li, Na or K.

The reaction is carried out in water or organic solvents at temperatures of 0° to 100° C., preferably at room temperature.

The invention furthermore relates to a process for the preparation of a salt of the formula (II) in which M$^{a+}$ denotes a silver, magnesium, copper(I), copper(II), zinc(II) or calcium(II) cation or an organic cation by a saltexchange reaction, characterised in that an alkali metal salt of the formula (II), prepared as described above or the acid itself, is reacted with a compound of the formula (III)

$$MA \quad (III),$$

where

M denotes a silver, magnesium, copper(I), copper(II), zinc(II) or calcium(II) cation or an organic cation and A=OH$^-$, F$^-$, Cl$^-$, Br$^-$, I$^-$, [HF$_2$]$^-$, [CN]$^-$, [SCN]$^-$, [CH$_3$COO]$^-$, [CH$_3$ SO$_3$]$^-$, [CF$_3$ COO]$^-$, [CF$_3$ SO$_3$]$^-$, [CH$_3$OSO$_3$]$^-$, [BF$_4$]$^-$, [SO$_4$]$^{2-}$, [HSO$_4$]$^{1-}$, [NO$_3$]$^-$, [C$_2$H$_5$OSO$_3$]$^-$, [(C$_2$F$_5$)$_2$P(O)O]$^-$, [C$_2$F$_5$P(O)O$_2$]$^{2-}$, tosylates, malonates, substituted malonates or [CO$_3$]$^{2-}$.

If the acids are employed, the reaction can also be carried out with metal oxides, for example oxides of the group 1, 2, 11 and 12 metals.

The anion of the formula (III) is preferably OH⁻, Cl⁻, Br⁻, I⁻, [CH₃SO₃]⁻ [CH₃OSO₃]⁻, [CF₃COO]⁻, [CF₃SO₃]⁻, [(C₂F₅)₂P(O)O]⁻ or [CO₃]²⁻, particularly preferably OH⁻, Cl⁻, Br⁻, [CH₃OSO₃]⁻, [CF₃SO₃]⁻, [CH₃SO₃]⁻ or [(C₂F₅)₂P(O)O]⁻.

The reaction is advantageously carried out in water, where temperatures of 0-100° C., preferably 15°-60° C., particularly preferably at room temperature, are suitable.

However, the reaction may alternatively also be carried out in organic solvents at temperatures between −30° and 100° C. Suitable solvents here are benzene, acetonitrile, dioxane, dichloromethane, dimethoxyethane, dimethyl sulfoxide, tetrahydrofuran, dimethylformamide or alcohol, for example methanol, ethanol or isopropanol.

The invention furthermore relates to the use of an acid of the formula (I) or of the formula (Ia), as described above, or of a salt of the general formula (II), as described above, for the synthesis of catalysts containing rare earths.

Catalysts containing rare earths or (transition) metals, such as, for example, rhodium, ruthenium, iridium, palladium, platinum, osmium, cobalt, nickel, iron, titanium, zirconium, hafnium, thorium, uranium, gold or tungsten, are important catalysts for reactions such as, for example, the catalytic hydrogenation of alkenes, hydroformylations, hydrosilylations, isomerisations of unsaturated compounds, carbonylations, C—C couplings, polymerisations or oligomerisations.

For the preparation of the rhodium catalysts of the formula (IV)

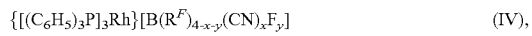

$$\{[(C_6H_5)_3P]_3Rh\}[B(R^F)_{4-x-y}(CN)_xF_y] \quad (IV),$$

where
x=1, 2 or 3,
y=0 or 1,
x+y≦4
and in which
the ligands $R^F$ may be identical or different and
$R^F$ stands for a perfluorinated or partially fluorinated $C_{1-12}$-alkyl group and where the CN group is bonded to the B atom via the C atom, an alkali metal salt of the formula (II), as described above, is reacted with $\{[(C_6H_5)_3)P]_3Rh\}Cl$.

A ligand exchange of chloride by the corresponding borate anion takes place here. The reaction is carried out in a polar solvent, preferably in an alcohol, such as ethanol or isopropanol, at temperatures between 0° C. and 100° C., preferably between 10° and 60° C., particularly preferably at room temperature. The rhodium catalysts formed can be purified by methods which are known to the person skilled in the art, such as, for example, by extraction and/or recrystallisation.

For the preparation of the Zr catalysts of the formula (V)

$$[Cp_2ZrCH_3][B(R^F)_{4-x-y}(CN)_xF_y] \quad (V),$$

where
x=0, 1, 2, 3 or 4,
y=0, 1, 2 or 3,
x+y≦4
Cp=cyclopentadienyl
and in which
the ligands $R^F$ may be identical or different and
$R^F$ stands for a perfluorinated or partially fluorinated $C_{1-12}$-alkyl group and where the CN group is bonded to the B atom via the C atom, an acid of the formula (I), as described above, optionally in the solvated form, is reacted with $Cp_2Zr(CH_3)_2$.

The reaction is advantageously carried out in dichloromethane. The starting materials are mixed at temperatures of −60° C., the actual reaction is carried out at room temperature. This type of catalyst is usually generated in situ.

The complete disclosure content of all applications, patents and publications mentioned above and below is incorporated into this application by way of reference.

Even without further comments, it is assumed that a person skilled in the art will be able to utilise the above description in its broadest scope. The pre-ferred embodiments and examples should therefore merely be regarded as descriptive disclosure which is absolutely not limiting in any way.

It goes without saying to the person skilled in the art that substituents, such as, for example, H, N O, Cl, F, in the compounds mentioned above and below may be replaced by the corresponding isotopes.

The NMR spectra were measured on solutions in deuterated solvents at 20° C. in a Bruker Avance 300 spectrometer with a 5 mm ¹H/BB broadband head with deuterium lock, unless indicated in the examples. The measurement frequencies of the various nuclei are: ¹H: 300.13 MHz, ¹¹B: 96.92 MHz, ¹⁹F: 282.41 MHz and ³¹P: 121.49 MHz. The referencing method is indicated separately for each spectrum or each data set.

EXAMPLES

Example 1

Synthesis of tris(trifluoromethyl)cyanoboric acid

1st step 113 mg (0.4 mmol) of K[(CF₃)₃BCN](synthesis is described in Example 5) are weighed out in a glass finger with a valve with a PTFE spindle in a dry box. 2 ml of trimethylsilyl iodide are condensed in at −196° C. on a vacuum apparatus. The reaction mixture is stirred at room temperature. After 10 hours, the excess trimethylsilyl iodide is removed in vacuo, and the residue is extracted with dichloromethane. The suspension is filtered through a glass frit covered with filter aid in an inert-gas atmosphere, and the solution is collected in a Schlenk flask. The reaction vessel and the frit are subsequently rinsed with dichloromethane. The solvent is removed in vacuo, and the residue is analysed by NMR. It is 95% [(CF₃)₃BCN]SiMe₃.

¹⁹F NMR spectrum, ppm (solvent: CD₂Cl₂; standard: CCl₃F—external): −60.7 q (CF₃).

¹H NMR spectrum, ppm (solvent: CD₂Cl₂; standard: TMS): 0.6 s (3CH₃).

¹¹B NMR spectrum, ppm (solvent: CD₂Cl₂; standard: BF₃.Et₂O/CD₃CN—external): −20.8 m; ²$J_{B,F}$=30 Hz.

2nd step 80 mg (0.25 mmol) of [(CF₃)₃BCN]SiMe₃ are introduced into a flask in a dry box. 5 ml of anhydrous HF are condensed in at −196° C. in vacuo with stirring on a stainless-steel apparatus. The reaction mixture is subsequently stirred at room temperature for one hour. All volatile constituents are pumped off, giving tris(trifluoromethyl)cyanoboric acid, [(CF₃)₃BCN]H, in a yield of 90%.

¹⁹F NMR spectrum, ppm (solvent: CD₂Cl₂; standard: CCl₃F—external): −60.4 q (CF₃)

¹H NMR spectrum, ppm (solvent: CD₂Cl₂; standard: TMS): 9.0 br.s (CNH).

¹¹B NMR spectrum, ppm (solvent: CD₂Cl₂; standard: BF₃.Et₂O/CD₃CN—external): −20.7 m; ²$J_{B,F}$=30 Hz.

Example 2

Synthesis of tris(trifluoromethyl)cyanoboric acid etherate [(CF₃)₃BCN]H*Et₂O 109 mg (0.39 mmol) of K[(CF₃)₃BCN]are weighed out into a glass finger with a valve with a PTFE spindle. 5 ml of diethyl ether followed by 0.9 mmol of HCl are condensed in at −196° C. in vacuo. The reaction mixture is stirred at room temperature for several hours. Immediately after warming, a colourless solid starts to precipitate. All volatile constituents are removed in vacuo. The residue is taken up in dichloromethane. The solid is filtered through a glass frit covered with filter aid in an $N_2$ atmosphere. The solution is evaporated, leaving a solid, giving tris(trifluoromethyl)cyanoboric acid etherate in a yield of 61%.

$^{19}$F NMR spectrum, ppm (solvent: $CD_2C_2$; standard: $CCl_3F$—external): −61.6 q ($CF_3$).

$^1$H NMR spectrum, ppm (solvent: $CD_2Cl_2$; standard: TMS): 13.5 br.s (CNH).

$^{11}$B NMR spectrum, ppm (solvent: $CD_2Cl_2$; standard: $BF_3 \cdot Et_2O/CD_3CN$—external): −21.8 m; $^2J_{B,F}$=30 Hz.

Example 3

Synthesis of [(CF$_3$)$_4$B]H*2 Et$_2$O 546 mg (1.68 mmol) of K[B(CF$_3$)$_4$] are weighed out into a flask with valve and PTFE spindle and carefully dried in vacuo. 80 ml of diethyl ether are condensed in, and the flask is cooled to −50° C. The solution is stirred continuously during the reaction. About 12 mmol of HCl are condensed into a second flask with valve with PTFE spindle at room temperature. The valves in the two flasks are opened. Only a few minutes after the gaseous HCl is brought into contact with the diethyl ether solution, white solid precipitates out of the solution. The temperature of the solution is set lower than −20° C. After 5 hours, all volatile substances are removed in vacuo. Anhydrous dichloromethane is added to the white residue with nitrogen through a PFA cannula. The suspension is filtered through a Celite-packed Schlenk frit, giving a clear solution. Dichloromethane is removed in vacuo, and [(CF$_3$)$_4$B]H*2 Et$_2$O is transferred into a dry box, giving 530 mg, which corresponds to a yield of 73%.

$^{19}$F NMR spectrum, ppm (solvent: $CD_2Cl_2$; standard: $CCl_3F$—internal): −61.6 q ($CF_3$), $^2J_{B,F}$=25.9 Hz.

$^1$H NMR spectrum, ppm (solvent: $CD_2Cl_2$; standard: TMS): 1.44 t (12H), $^3J_{H,H}$=7.16 Hz, 4.11 q (8H), $^3J_{H,H}$=7.16 Hz, 16.25 s (1H).

$^{11}$B NMR spectrum, ppm (solvent: $CD_2Cl_2$; standard: $BF_3 \cdot Et_2O/CD_3CN$—external): −18.9 m; $^2J_{B,F}$=25.9 Hz.

Example 4

Synthesis of Tetracyanoboric Acid Monohydrate

1st step:

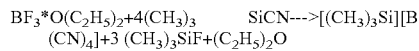

100 ml (86.3 g, 0.87 mol) of trimethylsilyl cyanide are reacted with 12 ml (13.1 g, 0.092 mol) of boron trifluoride etherate in a flask with exclusion of moisture. The solution becomes slightly warm. After 15 minutes, the reaction mixture is warmed at 30-40° C. for 18 hours, during which a solid precipitates. The product is filtered off with exclusion of moisture and washed successively with 10 ml of chloroform, 10 ml of toluene and 20 ml of pentane. Drying in vacuo gives 3.5 g (0.018 mol) of [(CH$_3$)$_3$Si][B(CN)$_4$], which corresponds to a yield of 20%.

2nd step:

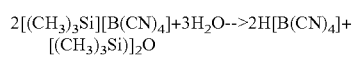

3.5 g of [(CH$_3$)$_3$Si][B(CN)$_4$] are reacted with 60 ml of water with ice-cooling. Two phases form, comprising an aqueous solution and [(CH$_3$)$_3$Si)]$_2$O. The aqueous solution is separated off and evaporated in vacuo. 80 ml of dichloromethane and 40 ml of diethyl ether are condensed onto the residue. The solution is filtered and evaporated in vacuo. The etherate formed is dissolved in 20 ml of water and evaporated in vacuo. The addition of water with subsequent evaporation is repeated twice more. The product formed in this way is dried for 20 hours in vacuo (10-3 mbar), giving 2.115 g (0.016 mol) of tetracyanoboric acid monohydrate, H[B(CN)$_4$]*H$_2$O, which corresponds to a yield of 17%.

$^1$H NMR spectrum, ppm (solvent: $CD_3CN$; standard: TMS): 10.3 s (1H).

$^{11}$B NMR spectrum, ppm (solvent: $CD_3CN$; standard: $BF_3 Et_2O$—external): −38.6 m; $^2J_{C,B}$=71.1 Hz.

Elemental analysis:

| | | | |
|---|---|---|---|
| calculated H$_3$C$_4$BN$_4$O | C: 35.88% | H: 2.26% | N: 41.84% |
| found: | C: 35.69% | H: 2.96% | N: 42.14%. |

Example 5

Synthesis of K[(CF$_3$)$_3$BCN]

1st step: Synthesis of tris(trifluoromethyl)isocyanoboric acid 2.04 g (8.3 mmol) of carbonyltris(trifluoromethyl)borane, 20 ml of dichloromethane and 13.1 mmol of HCN are condensed at −196° C. into a flask with a valve and a PTFE spindle on a vacuum apparatus. The reaction mixture is warmed to −80° C. and warmed to room temperature overnight with stirring. All volatile constituents are removed in vacuo, giving 1.94 g (7.9 mmol) of tris(trifluoromethyl)isocyanoboric acid [(CF$_3$)$_3$BNC]H, which corresponds to a yield of 95%.

Elemental analysis:

| | | | |
|---|---|---|---|
| calculated C4HBF9N | C: 19.62% | H: 0.41% | N: 5.72% |
| found: | C: 19.80% | H: 0.40% | N: 5.80%. |

2nd step: Synthesis of K[(CF$_3$)$_3$BNC]

1.12 g (4.6 mmol) of tris(trifluoromethyl)isocyanoboric acid, prepared as described in Example 1, are weighed out into a Schlenk finger with a valve with a PTFE spindle in a dry box, and a dropping funnel is attached. A flask with a valve with a PTFE spindle is filled, likewise in a dry box, with 1.92 g (11.5 mmol) of Li[N(SiMe$_3$)$_2$]. The two solids are each dissolved in 40 ml of toluene on a vacuum apparatus. The solution of the amide is transferred into the dropping funnel. The reaction vessel is cooled to −20° C., and the toluene/amide solution is added dropwise over the course of two hours with stirring. When the addition is complete, the reaction mixture is stirred at −20° C. for a further 30 minutes. 20 ml of an aqueous KOH/K$_2$CO$_3$ solution are subsequently added to the mixture. The toluene phase is separated off, and the solvent is removed in vacuo in a rotary evaporator. The residue is taken up in 50 ml of diethyl ether and added to the aqueous phase of the reaction. The reaction mixture is extracted with a further 100 and 50 ml of diethyl ether. The combined organic phases are dried using potassium carbonate, and the mixture is subsequently filtered. All volatile constituents are pumped off on a rotary evaporator, giving 1.08 g of potassium tris(trifluoromethyl)isocyanoborate, which corresponds to a yield of 83%.

$^{19}$F NMR spectrum, ppm (solvent: acetonitrile-D$_3$; standard: CCl$_3$F—external): −67.0 q (CF$_3$).

$^{11}$B NMR spectrum, ppm (solvent: acetonitrile-D$_3$; standard: BF$_3$.Et$_2$O CD$_3$CN—external): −17.5 m; $^2J_{B,F}$=29 Hz.

$^{13}$C NMR spectrum, ppm (solvent: acetonitrile-D$_3$; standard: TMS): 131.7 q (CF$_3$); 172.3 s (NC); $^1J_{C,F}$=305 Hz.

Elemental analysis:

| | | |
|---|---|---|
| calculated C$_4$BF$_9$KN | C: 16.98% | N: 4.95% |
| found: | C: 17.11% | N: 5.10%. |

3rd step: Synthesis of K[(CF$_3$)$_3$BCN]

515 mg (1.8 mmol) of potassium tris(trifluoromethyl)isocyanoborate is heated to 240° C. in a heating chamber at a heating rate of 10 K min-1 and conditioned at 200-240° C. for a further 10 minutes. During the isomerisation, the heating chamber is continuously flushed with nitrogen. The salt is sub-sequently cooled to room temperature, giving 515 mg of potassium tris(trifluoromethyl)cyanoborate).

$^{19}$F NMR spectrum, ppm (solvent: acetonitrile-D$_3$; standard: CCl$_3$F—external): −62.1 q (CF$_3$).

$^{11}$B NMR spectrum, ppm (solvent: acetonitrile-D$_3$; standard: BF$_3$.Et$_2$O/CD$_3$CN—external): −22.3 m; $^2J_{B,F}$=29 Hz.

$^{13}$C NMR spectrum, ppm (solvent: acetonitrile-D$_3$; standard: TMS): 132.4 q (CF$_3$); 127.5 s (CN); $^1J_{C,F}$=303 Hz.

Elemental analysis:

| | | |
|---|---|---|
| calculated C$_4$BF$_9$KN | C: 16.98% | N: 4.95% |
| found: | C: 16.79% | N: 4.97%. |

Example 6

Synthesis of [C(NH$_2$)$_3$][(CF$_3$)$_3$BCN]

A solution of 2.50 g (8.8 mmol) of K[(CF$_3$)$_3$BCN]in 150 ml of ethanol is added with stirring to a solution of 1.37 g (14.3 mmol) of guanidinium chloride in 150 ml of ethanol. The mixture is stirred at room temperature for one hour, and the ethanol is subsequently distilled off. The colourless residue is extracted twice with THF. The THF solution is filtered, and the solvent is removed in vacuo, giving 2.55 g (8.4 mmol) of guanidinium tris(trifluoromethyl)cyanoborate, which corresponds to a yield of 95%.

$^{19}$F NMR-spectrum, ppm (solvent: acetonitrile-D$_3$; standard: CCl$_3$F—external): −62.0 q (CF$_3$).

$^{11}$B NMR spectrum, ppm (solvent: acetonitrile-D$_3$; standard: BF$_3$.Et$_2$O/CD$_3$CN—external): −22.3 m; $^2J_{B,F}$=29 Hz.

$^1$H NMR spectrum, ppm (solvent: acetonitrile-D$_3$; standard: TMS): 6.1 br. s (NH).

Example 7

Synthesis of [Ph$_3$C][(CF$_3$)$_3$BCN]

312 mg (1.1 mmol) of K[(CF$_3$)$_3$BCN] and 323 mg (1.2 mmol) of triphenylmethyl chloride are weighed out into a flask with a valve with a PTFE spindle. The traces of water are removed thoroughly in vacuo. 100 ml of anhydrous dichloromethane are added to the solids in an inert-gas atmosphere. The suspension is stirred overnight. In an inert-gas atmosphere, the suspension is filtered through a Schlenk frit covered with filter aid and collected in a flask. The reaction flask is rinsed twice with dichloromethane (20 ml, ml). The liquid is subsequently filtered through the frit. The dichloromethane solution is concentrated to a volume of about 2 ml in vacuo. The trityl salt is precipitated as solid by slow addition of 25 ml of hexane with constant stirring. After one hour, the stirring is stopped, and the product settles. The liquid phase is removed. The crude product is washed with hexane, giving 445 mg of triphenylmethyl tris(trifluoromethyl)cyanoborate, which corresponds to a yield of 82%.

Elemental analysis:

| | | | |
|---|---|---|---|
| calculated C$_{23}$H$_{15}$BF$_9$N | C: 56.71% | H: 3.10% | N: 2.88% |
| found: | C: 55.85% | H: 3.15% | N: 2.98%. |

Example 8

Synthesis of {(PPh$_3$)Rh}[NCB(CF$_3$)$_3$], Ph=phenyl 72 mg (0.26 mmol) of K[(CF$_3$)$_3$BCN]and 205 mg (0.22 mmol) of {(PPh$_3$)$_3$Rh}Cl are introduced into a reaction vessel in a dry box. 20 ml of dried ethanol are condensed in at −196° C. with stirring. The reaction mixture is warmed to room temperature and stirred for three days. The solvent is removed in vacuo. In an inert-gas atmosphere, the orange residue is extracted twice with methylene chloride. The fine white solid of inorganic salt is separated off from the solution by filtration. The dichloromethane is removed in vacuo, giving 227 mg (0.20 mmol) of rhodium catalyst (PPh$_3$)RhNCB(CF$_3$)$_3$, which corresponds to a yield of 91%.

$^{19}$F NMR spectrum, ppm (solvent: acetonitrile-D$_3$; standard: CCl$_3$F—external): −60.7 br.s. (CF$_3$).

$^{11}$B NMR spectrum, ppm (solvent: acetonitrile-D$_3$; standard: BF$_3$.Et$_2$O/CD$_3$CN—external): −22.2 br.s.

$^{31}$P NMR spectrum, ppm (solvent: acetonitrile-D$_3$; standard: 85% H$_3$PO$_4$-external): 44.2 d,t (trans); 30.6 d,d (cis); $^1J_{P,Rh}$ (trans)=178 Hz; $^1J_{P,Rh}$ (cis)=138 Hz.

Example 9

Synthesis of [Cp$_2$ZrMe(OEt$_2$)][B(CF$_3$)$_4$], Cp=cyclopentadienyl, Me=methyl, Et=ethyl 86 mg (0.20 mmol) of [H(OEt$_2$)$_2$][B(CF$_3$)$_4$]and 47 mg (0.19 mmol) of Cp$_2$ZrMe$_2$ are mixed at −196° C.

After the reaction mixture has been warmed to −60° C., gas evolution commences and a solid precipitates. After 12 hours at room temperature, all volatile constituents are removed in vacuo, giving [Cp$_2$ZrMe(OEt$_2$)][B(CF$_3$)$_4$].

$^{19}$F NMR spectrum, ppm (solvent: CD$_2$Cl$_2$; standard: CCl$_3$F—external): −61.6 q (CF$_3$).

$^{11}$B NMR spectrum, ppm (solvent: CD$_2$Cl$_2$; standard: BF$_3$.Et$_2$O/CD$_3$CN—external): −18.9 m; $^2J_{B,F}$=26 Hz.

$^1$H NMR spectrum, ppm (solvent: CD$_2$Cl$_2$; standard: TMS): 0.84 br.s. (CH$_3$); 1.24 t (2CH$_3$); 3.68 m (2CH$_2$); 6.46 br.s. (C$_5$H$_5$); $^3J_{H,H}$=7.0 Hz.

The invention claimed is:

1. A salt of formula (II)

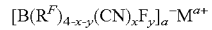   (II)

where
x=1, 2 or 3,
y=0 or 1,
x+y<4,
a=1 or 2,
and in which
the ligands $R^F$ may be identical or different and $R^F$ stands for a perfluorinated or partially fluorinated $C_{1-12}$-alkyl group and where the CN group is bonded to the B atom via the C atom, and $M^{a+}$ is an alkali metal cation, a silver, magnesium, copper (I), copper(II), zinc(II) or calcium(II) cation or an organic cation,
with the exception of $K[B(CF_3)_3CN]$ and $[NH_4][B(CF_3)_3CN]$.

2. A salt according to claim 1, wherein $M^{a+}$ is an alkali metal cation.

3. A salt according to claim 1, wherein $M^{a+}$ is an organic cation which is $[NR^1R^2R^3R^4]^+$, $[PR^1R^2R^3R^4]^+$, $[P(NR^1R^2)_2(NR^3R^4)_2]^+$, $C(NR^1R^2)(NR^3R^4)(NR^5R^6)]^+$, $[(R^1R^2N)—C(=OR^7)(NR^3R^4)]^+$ or $[(R^1R^2N)—C(=SR^7)(NR^3R^4)]^+$, in which $R^1$ to $R^7$ each, independently of one another, denotes
hydrogen,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
where one or more of the substituents $R^1$ to $R^7$ may be partially or fully substituted by halogens, or partially by —CN or —NO₂, and
where, in the substituents $R^1$ to $R^6$, one or two non-adjacent carbon atoms which are not in the α-position may be replaced by atoms and/or atom groups selected from the group consisting of —O—, —C(O)—, —C(O)O—, —S—, —S(O)—, —SO₂—, —SO₂O—, —C(O)NH—, —C(O)NR'—, —SO₂NH—, —SO₂NR'—, —N═, —N═N—, —NH—, —NR'—, —PR'—, —P(O)R'—, —P(O)R'—O—, —O—P(O)R'—O—, —P(O)(NR'₂)—NR'— and —PR'₂═N— and by the end groups —C(O)X' and —SO₂X',
where R'=non-, partially or perfluorinated $C_1$- to $C_6$-alkyl, $C_3$- to $C_7$-cycloalkyl, unsubstituted or substituted phenyl or an unsubstituted or substituted heterocycle, and X'=F, Cl or Br.

4. A salt according to claim 1, wherein the organic cation in $M^{a+}$ is a heterocyclic cation which is

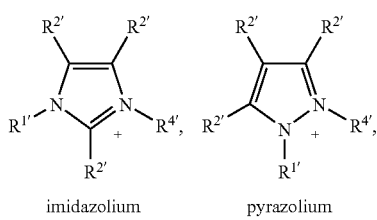

imidazolium     pyrazolium

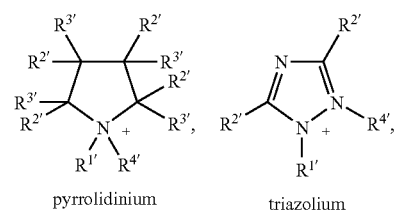

pyrrolidinium     triazolium

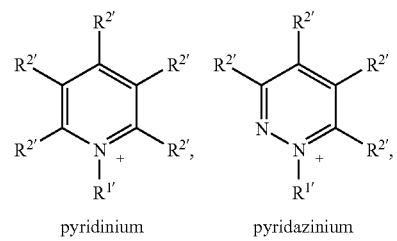

pyridinium     pyridazinium

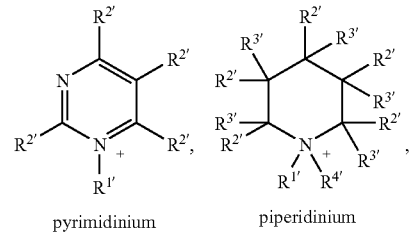

pyrimidinium     piperidinium

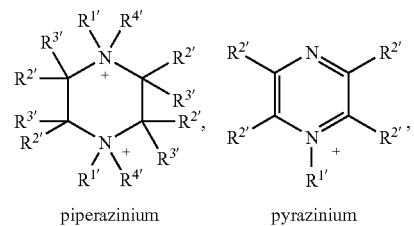

piperazinium     pyrazinium

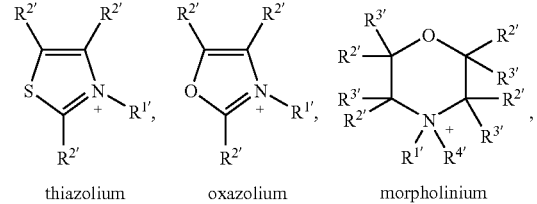

thiazolium     oxazolium     morpholinium

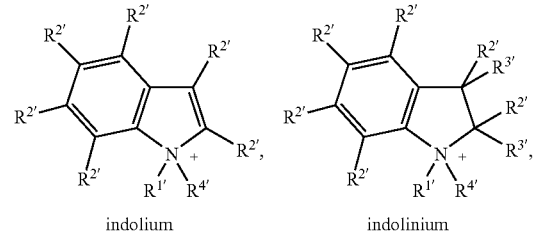

indolium     indolinium

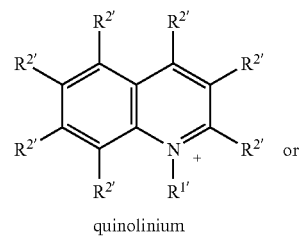

quinolinium     or

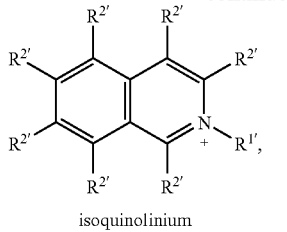

isoquinolinium where
R$^{1'}$ to R$^{4'}$ each, independently of one another, denotes
hydrogen,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms,
saturated, partially or fully unsaturated heteroaryl, heteroaryl-C$_1$-C$_6$-alkyl or aryl-C$_1$-C$_6$-alkyl,
where one or more substituents R$^{1'}$ to R$^{4'}$ may be partially or fully substituted by halogens, or partially by —CN or —NO$_2$,
where R$^{1'}$ and R$^{4'}$ cannot simultaneously be perfluorinated or perchlorinated, and
where, in the substituents R$^{1'}$ to R$^{4'}$, one or two non-adjacent carbon atoms which are not in the α-position to the heteroatom may be replaced by atoms and/or atom groups selected from the group consisting of —O—, —C(O)—, —C(O)O—, —S—, —S(O)—, —SO$_2$—, —SO$_2$O—, —C(O)NH—, —C(O)NR'—, —SO$_2$NH—, —SO$_2$NR'—, —N=, —N=N—, —NH—, —NR'—, —PR'—, —P(O)R'—, —P(O)R'—O—, —O—P(O)R'—O—, —P(O)(NR'$_2$)—NR'— and —PR'$_2$=N— and by the end groups —C(O)X' and —SO$_2$X',
where R'=non-, partially or perfluorinated C$_1$- to C$_6$-alkyl, C$_3$- to C$_7$-cycloalkyl, un-substituted or substituted phenyl or an unsubstituted or substituted heterocycle, and X'=F, Cl or Br.

5. A process for preparing a salt of formula (II) according to claim 1 in a salt-exchange reaction, comprising reacting an alkali metal salt of formula (II) wherein M$^{a+}$ is an alkali metal cation
with a compound of the formula (III)

$$MA \qquad (III),$$

where
M denotes a silver, magnesium, copper(I), copper(II), zinc (II) or calcium(II) cation or an organic cation and
A denotes OH$^-$, F$^-$, Cl$^-$, Br$^-$, I$^-$, [HF$_2$]$^-$, [CN]$^-$, [SCN]$^-$, [CH$_3$COO]$^-$, [CH$_3$SO$_3$]$^-$, [CF$_3$COO]$^-$, [CF$_3$SO$_3$]$^-$, [CH$_3$OSO$_3$]$^-$, [BF$_4$]$^-$, [SO$_4$]$^{2-}$, [NO$_3$]$^-$, [C$_2$H$_5$OSO$_3$]$^-$, [(C$_2$F$_5$)$_2$P(O)O]$^-$, [C$_2$F$_5$P(O)O$_2$]$^{2-}$, a tosylate, a malonate, a substituted malonate or [CO$_3$]$^{2-}$.

\* \* \* \* \*